United States Patent [19]

Fishel et al.

[11] 4,035,428
[45] July 12, 1977

[54] PROCESS FOR PRODUCTION OF ORTHOPHENYLPHENOL

[75] Inventors: Norman A. Fishel, Olivette; David E. Gross, St. Charles, both of Mo.

[73] Assignee: Monsanto Company, St. Louis, Mo.

[21] Appl. No.: 603,064

[22] Filed: Aug. 8, 1975

[51] Int. Cl.² .......................................... C07C 37/00
[52] U.S. Cl. ........................ 260/620; 260/346.2 M
[58] Field of Search .................... 260/620, 346.2 M

[56] References Cited

U.S. PATENT DOCUMENTS

| | | | |
|---|---|---|---|
| 1,808,349 | 6/1931 | Hale et al. | 260/346.2 M |
| 2,244,244 | 6/1941 | Deseke | 260/620 |
| 2,862,035 | 11/1958 | Muller et al. | 260/620 |
| 3,897,453 | 7/1975 | Ganto | 260/346.2 M |
| 3,898,289 | 8/1975 | Schneider | 260/620 |

OTHER PUBLICATIONS

Shurkin et al., "J. Gen. Chem. USSR", vol. 29, pp. 2932–3935, (1959).

*Primary Examiner*—Norman Morgenstern
*Attorney, Agent, or Firm*—Joseph D. Kennedy; John D. Upham

[57] ABSTRACT

A process for production of orthophenylphenol is disclosed. More specifically, the invention relates to the conversion of phenol or diphenyl ether into orthophenylphenol in a two-stage process in which dibenzofuran is an intermediate.

14 Claims, 1 Drawing Figure

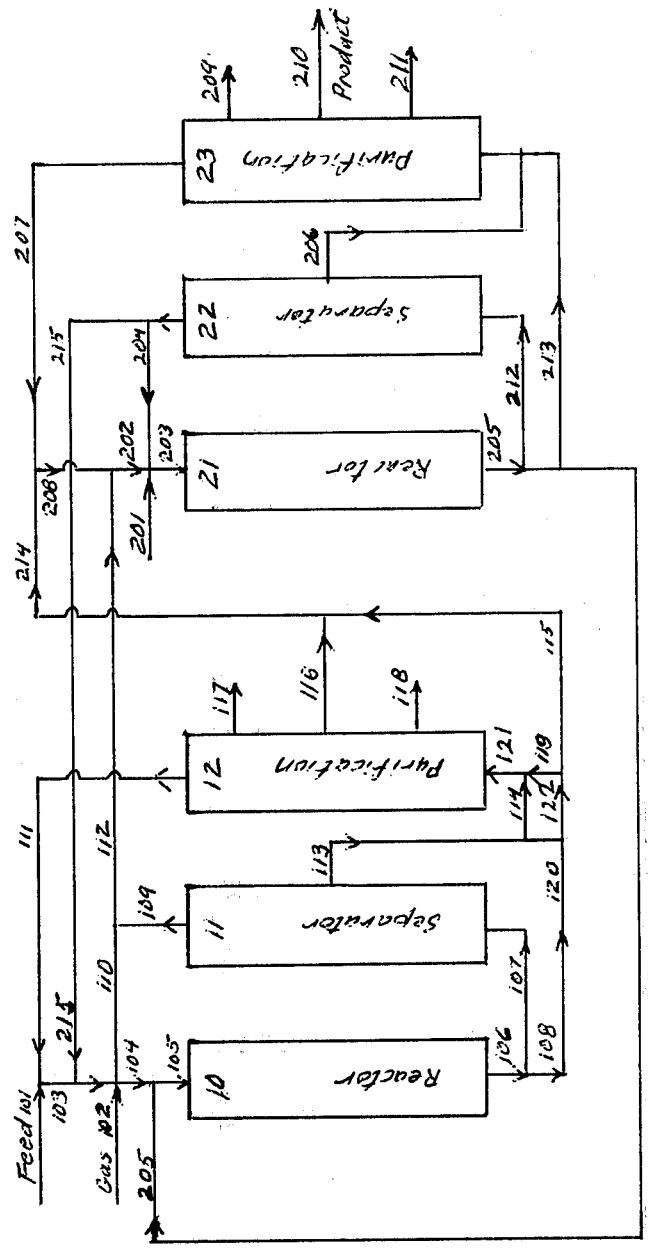

PROCESS FOR PRODUCTION OF ORTHOPHENYLPHENOL

BACKGROUND OF THE INVENTION

1. Field of the Invention

The present invention relates to a novel process for preparation of orthophenylphenol. More particularly, this invention relates to a process in which phenol is subjected to a dehydration-dehydrogenation step to yield dibenzofuran which is subsequently subjected to a hydrogenolysis reaction to yield orthophenylphenol. It is also contemplated within the scope of the present invention to use diphenyl ether as a feedstock which is subjected to a dehydrogenation step to yield dibenzofuran which is subsequently subjected to a hydrogenolysis reaction to yield orthophenylphenol.

2. Prior Art

There is a demand for orthophenylphenol because it has been found useful as an antimicrobial agent, in the preparation of dyestuffs, as a preservative, and other useful applications, Orthophenylphenol for commercial use is presently obtained, for example, by processes employing caustic hydrolysis of aryl halides or by self-condensation of cyclohexanone followed by a dehydrogenation step. The art also shows teachings showing many other methods of synthesis of orthophenylphenol, none of which however are believed to be attractive for commercial production of orthophenylphenol by reason of high costs, low yields, or presence of impurities for example.

STATEMENT OF THE INVENTION

It has now been discovered that orthophenylphenol may be produced economically in a process wherein phenol is converted into orthophenylphenol in a two-stage process in which dibenzofuran is an intermediate. It has also been discovered that orthophenylphenol may be produced economically in a process wherein diphenyl ether is converted into orthophenylphenol in a two-stage process in which dibenzofuran is an intermediate.

It is an advantage of the instant process in that essentially only the ortho isomer of phenylphenol is produced, thereby obviating the need to provide a means for separation of the phenylphenol isomers or their precursors as may be required in processes employing the caustic hydrolysis of aryl halides. Another advantage of the instant process is that most of the difficulties encountered in the cyclohexanone self-condensation process to separate orthophenylphenol from its saturated or partially saturated precursors are overcome.

Accordingly, it is an important object of the present invention to provide a process for production of orthophenylphenol from phenol.

Another object of this invention is to provide a process for production of orthophenylphenol from diphenyl ether.

Still another important object is to provide a process for production of orthophenylphenol in which dibenzofuran is an intermediate.

These and other objects and advantages of the present invention will become apparent from inspection of the following detailed description which covers several preferred embodiments of the invention.

DESCRIPTION OF THE PREFERRED EMBODIMENTS

The objects of the present invention may be accomplished by preparing a product stream containing orthophenylphenol. The method of this invention for preparing a product stream containing orthophenylphenol may typically comprise passing a charge stream containing phenol into contact with a dehydration-dehydrogenation catalyst at dehydration-dehydrogenation conditions, thereby forming a stream containing dibenzofuran; separating dibenzofuran and unreacted phenol from the aforementioned dibenzofuran containing stream; returning the unreacted phenol recovered from the dibenzofuran stream to the dehydration-dehydrogenation reactor; passing the recovered dibenzofuran along with hydrogen into contact with a hydrogenolysis catalyst at hydrogenolysis conditions, thereby forming a stream containing orthophenylphenol; separating the orthophenylphenol and unreacted dibenzofuran from the orthophenylphenol-containing stream; returning the unreacted dibenzofuran recovered form the orthophenylphenol stream to the hydrogenolysis reactor; and recovering the orthophenylphenol separated from the orthophenylphenol stream.

Other objects of the present invention may be accomplished by preparing a product stream containing orthophenylphenol in the following manner. A charge stream containing diphenyl ether is passed into contact with a dehydrogenation catalyst at dehydrogenation conditions, thereby forming a stream containing dibenzofuran; separating dibenzofuran and unreacted diphenyl ether from the dibenzofuran containing stream; returning the unreacted diphenyl ether recovered from the dibenzofuran containing stream to the dehydrogenation reactor; passing the recovered dibenzofuran along with hydrogen into contact with a hydrogenolysis catalyst at hydrogenolysis conditions, thereby forming a stream containing orthophenylphenol; separating the orthophenylphenol and unreacted dibenzofuran from the orthophenylphenol containing stream; returning the unreacted dibenzofuran recovered from the orthophenylphenol stream to the hydrogenolysis reactor; and recovering the orthophenylphenol separated from the orthophenylphenol stream.

One embodiment of this invention is illustrated in the drawing which is a schematic representation of a two-stage process for production of orthophenylphenol in which dibenzofuran is an intermediate.

The charge to the process in line 101, for example, includes phenol and diphenyl ether which may be mixed with hydrogen and other suitable gases admitted through line 102; and the mixture is passed through lines 104 and 105 to the dehydration-dehydrogenation operation 10. The catalyst in operation 10 is operated at conditions to produce dibenzofuran. Effluent leaving operation 10 through line 106 may either be directed wholly or in part through line 107 to a gas-liquid separation operation 11 or may be directed wholly or in part through line 108. A gas phase stream may be withdrawn from operation 11 through line 109 and may be passed either wholly or in part through lines 110 and 112. The gases directed through line 110 may be mixed with materials from lines 102 and 103 to form a gas stream in line 104 which is directed to the inlet of operation 10. A liquid phase stream may be withdrawn from operation 11 through line 113 and may be passed either wholly or in part through lines 114 and 120.

The charge to separation operation 12 admitted through line 121 consists of a stream from separation operation 11 admitted through lines 113 and 114 and a stream from operation 10 admitted through lines 106, 108, 122, and 119. The diversity of lines allows the effluent of operation 10 to be directed to either separation operation 11 or separation operation 12 or both or neither depending upon the nature of the effluent stream in line 106.

The separation operation 12 may be operated in a manner such that withdrawn from the operation is stream 111 which may be recycled back to operation 10 and combined with fresh feedstock. Also withdrawn from separation operation 12 may be stream 117 containing low boiling materials and stream 118 containing high boiling materials which may be disposed of in any suitable manner.

In addition a dibenzofuran-containing stream may be withdrawn from separation operation 12 through line 116, combined with the stream in line 115 and directed toward the inlet of operation 21.

The dibenzofuran-containing stream 214 may be combined with the gas stream in line 112 obtained from separation operation 11 and with hydrogen and other suitable gases admitted to the system through line 201 to form a charge mixture introduced through line 203 to the hydrogenolysis operation 21. The catalyst in operation 21 is operated at hydrogenolysis conditions to produce orthophenylphenol from the dibenzofuran introduced into operation 21. Effluent leaving operation 21 through line 205 may be directed wholly or in part through line 212 to separation operation 22; through line 213 to separation operation 23; or both, or neither, or through line 205 to the inlet of operation 10; or any suitable combination thereof depending upon the conditions of operation 21, the nature of the catalyst, and the nature of the feedstock. The product orthophenylphenol leaves through line 210.

A summary of the major lines is set forth below with the feed entering at 101, and the product being withdrawn from line 210:
101 Phenol or diphenyl ether feedstock
102 Hydrogen or nitrogen feed
103 Total liquid feedstock
104 Gas-liquid mixture
105 Inlet to reactor 10
106 Product from reactor 10
107 Inlet to gas-liquid separator 11
108 Reactor product to separation step 12
109 Gas outlet from gas-liquid separator 11
110 Gas recycle
111 Phenol or diphenyl ether recycle
112 Hydrogen from gas-liquid separator 11
113 Liquid from gas-liquid separator 11
114 Liquid to separation step 12
115 Liquid product from reactor 10 to separation step 12
116 Dibenzofuran
117 Light products
118 Heavy products
201 Hydrogen feed
202 Gas-liquid mixture to reactor 21
203 Inlet to reactor 21
204 Recycle hydrogen
205 Product from reactor 21
206 Liquid product from gas-liquid separator 22
207 Dibenzofuran recycle
208 Liquid feed to reactor 21
209 Light products
210 Orthophenylphenol product
211 Heavy products
212 Inlet to gas-liquid separator 22
213 Reactor product to separation 23
214 Reactor 10 product to reactor 21
215 Hydrogen recycle to reactor 10

Other objects and embodiments of the present invention relate to additional details regarding preferred catalytic ingredient amounts of components in the catalyst composite, suitable methods of composite preparation, operating conditions for use in the conversion processes and the like particulars which are hereinafter given in the following detailed discussion of the present invention.

The method for preparing a stream containing dibenzofuran may be accomplished by passing a charge stream containing phenol into contact with a catalyst comprised of cerium oxide at conditions such that both a dehydration and dehydrogenation reaction take place in a manner such that one molecule of water is released and an ether linkage formed between two molecules of phenol and one hydrogen molecule is released, one hydrogen atoms being removed from one ortho position of each phenol molecule, and a second link is formed between the two constituents at the aforesaid ortho positions to produce a five-membered ring oxide.

A catalyst is essential to effectively carry out the dehydration-dehydrogenation step to produce dibenzofuran, and as such, a material capable of catalyzing the dehydration and dehydrogenation of phenol must be used.

Another method for preparing a stream containing dibenzofuran may be accomplished by passing a charge stream containing diphenyl ether into contact with a catalyst comprised of cerium oxide at conditions such that a dehydrogenation reaction takes place in a manner such that one hydrogen molecule is released, one hydrogen atom being removed from one ortho position of each of the phenyl groups of diphenyl ether and a second link is formed between the two phenyl groups at the aforesaid ortho positions to produce a five-membered ring oxide. A catalyst is essential to effectively carry out the dehydrogenation step to produce dibenzofuran, and as such, a material capable of catalyzing the dehydrogenation of diphenyl ether must be used.

Cerium oxide, for example, has been found useful as a catalytic material for the dehydration and dehydrogenation of phenol and the dehydrogenation of diphenyl ether to yield dibenzofuran. Cerium oxide may be used in combination with other materials which are sufficiently refractory to withstand the elevated reaction temperature at which the reaction is preferably conducted. For example, oxides of aluminum, silicon, magnesium, titanium zirconium, hafnium, calcium, potassium, sodium, lanthanum, neodymium, praseodymium, samarium, thorium, and uranium as well as mixtures thereof may be used in combination with cerium oxide as the active catalytic material. The extent of desired reactions obtained by using less than 1% by weight of the cerium oxide is perceptible but not sufficient to be of any appreciable value. Cerium oxide which is essentially pure may be used as the active catalytic material. If desired the catalyst may be charged to the reactor as an oxide or converted to the oxide in situ prior to the dehydration and dehydrogenation reactions. In accordance with various practices of the art, the active catalyst may be used unsupported, or dispersed or supported on a suitable carrier material, such as alumina or silica alumina (e.g. 50–95% silica), supported or unsupported, in the reaction mixture which may include a solvent such as benzene, biphenyl, toluene or the like.

To produce a dibenzofuran containing stream, the reactants are introduced into the reaction vessel containing the catalyst which is maintained at a temperature high enough to vaporize the reactants and also high enough to induce a good reaction rate so that an adequate yield of the product may be obtained at reasonable space velocities as hereinafter described. On the other hand, it is preferred that the temperature should not be raised so high that the yield drops off or decomposition of the products or starting materials occurs. In general the reaction temperature is desirably above about 300° C or preferably from about 300° to 700° C. The preferred temperature range, however, will depend somewhat on the starting materials. In particular for phenol the reaction temperature is preferably above about 350° C with optimum results being obtained within the range of about 450° to 600° C. For diphenyl ether the reaction temperature is preferably above about 450° C with optimum results being obtained within the range of about 475° to 600° C. The temperature of the reaction chamber may be controlled in conventional manner to maintain the desired operating temperature.

Reaction pressure is not particularly critical, so subatmospheric, atmospheric, or superatmospheric pressures may be used according to desire. However, it is seldom desirable to raise the reaction pressure such that the process is converted into either a mixed phase or liquid phase reaction as opposed to the preferred vapor phase reaction. It is nonetheless contemplated within the scope of this invention that superatmospheric pressures up to about 150 atmospheres or higher may be employed. In the event that superatmospheric pressures are employed, the pressures may be provided by introducing into the reaction zone a gas such as water vapor, nitrogen or hydrogen, the amount of pressure which is employed being that which is sufficient to maintain a major portion of the reactants in the liquid phase while a minor portion are in the vapor phase, however, higher pressures may be used. On the other hand, the amount of gas which is employed may be limited to that which is sufficient to produce the desired superatmospheric pressure, however, the amount being less than that which produces condensation of the reactants. In general, atmospheric pressure is preferred for convenience, simplicity, and economy in carrying out the reaction.

It is contemplated within the scope of this invention that the process described herein may be effected in a continuous manner. One particular method comprises a fixed bed operation in which the reactant feed stream is continuously charged to a reactor containing a fixed bed of catalyst, the reactor being maintained, at the desired operating temperature, broadly 300° to 700° C, preferably about 400° to 600° C, thereby allowing the heated reactants to contact the catalyst. Other means of accomplishing a continuous operation are by using the catalyst in a moving bed system or fluidized bed system; however, in view of the well known operational advantages, it is preferred to use a fixed bed system. The reactor may be operated at subatmospheric, atmospheric, or superatmospheric pressure e.g. from 0.1 to 100 atmospheres, absolute. It is also contemplated that within the scope of the invention, gases such as water vapor, $N_2$ and $H_2$ as well as mixtures thereof may be continuously or intermittently charged to the reaction zone so long as the gases and reactants are preheated by any suitable means to the desired reaction temperature prior to introduction to the reaction zone. In general the proportion of water vapor is from 0 to equal proportions by weight relative to the feedstock, and the proportion of nitrogen or hydrogen is from 0.5 to 12 moles of the nitrogen or hydrogen per mole of the feedstock. The reactants may be passed over the catalyst bed in either upward or downward flow for example, and the products withdrawn continuously, allowed to cool, and recovered.

In the event it is desired to operate the reactor at subatmospheric or superatmospheric pressure conventional means for obtaining such condition, for example by use of mechanical vacuum pumps or mechanical compressors, may be employed.

The dibenzofuran containing stream which may contain dibenzofuran, unreacted feedstock, water, hydrogen, and other components depending upon for example, the reactivity of the starting material, the activity of the catalyst, and the reaction conditions, may then be subjected to an operation in which those components such as hydrogen, which are normally gases may be separated from those components such as dibenzofuran which may be liquids by conventional means such as a gas-liquid separator and then directed to various other operations as described in the present invention.

The dibenzofuran may be separated from other components such as unreacted feedstock by a separation operation which may consist of, for example, a conventional distillation or fractional crystallization. The dibenzofuran component may then be directed to the hydrogenolysis operation and the unreacted feedstock recycled to the inlet of the reactor containing the catalyst comprised of cerium oxide.

The method for preparing a stream containing orthophenylphenol may be accomplished by passing dibenzofuran recovered from the product stream from the reactor containing the catalyst comprised of cerium oxide, along with hydrogen into contact with a catalyst comprised of a Group VIII metal on a porous support at conditions such that a hydrogenolysis reaction takes place in a manner such that one of the carbon to oxygen bonds in the furan ring of dibenzofuran is selectively cleaved with subsequent addition of hydrogen to form the orthophenylphenol product, without substantially hydrogenating the unsaturated portion of the structure or without substantially cleaving the phenyl or phenyl linkage. A catalyst is essential to effectively carry out the hydrogenolysis step is a selective manner to produce orthophenylphenol from dibenzofuran.

The preferred catalyst for the hydrogenolysis operation of this invention is comprised of minor amounts of one or more Group VIII elements, in the range of about 0.01 to 49% by weight, and more preferably, with cost consideration for certain of the Group VIII elements, in the range of about 0.01 to 5% by weight, and may be on a support which is in the form of powders, granules, spheres, tablets, extrudates, and other forms thereof. It may be prepared for example by impregnating a porous support with a compound of a Group VIII element which is subsequently decomposed. Depending on the type of decomposition carried out for the compound, the active may be in one or more possible forms, for example, as an oxide, sulfide, hydride, or the zero valent metal.

Carbon can be used as a porous support for the catalyst and may be obtained from any suitable source whether animal, vegetable, or mineral. A suitable carbon for example, may be obtained from mineral sources, particularly from a brownish black coal, intermediate between peat and bituminous coal, commonly referred to by those skilled in the art as lignite. It will be readily appreciated by those skilled in the art of catalysis that the carbon have adequate absorptive powers, for this reason the carbon should preferably be activated. It may be activated by any suitable means, for instance, by a thermal oxidation such as steam treatment of the lignite. An example of a carbon obtained by activation from lignite is Darco 12×20 supplied by Atlas Chemical Industries, Inc.

Other porous supports may be used as the catalyst carrier for the process of this invention, such as magnesia, alumina, silica, titania, or the like and mixtures thereof.

These porous supports may be obtained from any suitable source that will provide a material having the desired purity. These catalyst carriers should be substantially free from substances or metals that are known or may prove to be poisons for the catalyst of the invention.

The surface area for these catalyst carriers may be in the range of about 1 to 10,000 m²/gram or higher, or preferably about 10 to 2,000 m²/gram.

A catalyst may typically be prepared, using the following method. An impregnation solution comprised of an appropriate amount of soluble Group VIII metal compound dissolved in distilled water, or other suitable solvent, and diluted to the desired volume, preferably in excess of the solution absorptivity of the support. The support is intermingled with said solution and the resulting mixture is stirred for about five minutes at ambient conditions followed by slow removal of water by stirring and passing a soft air flow over the preparation to give a free-flowing material. Further drying may be accomplished by mild heating. The still damp preparation is finally dried over a period of about 18 hours at about 120° C in a forced air oven.

The dried preparation may be reduced by any suitable method, for example, reduced in hydrogen gas at about 450° C for about 4 hours or chemically reduced using an aqueous formaldehyde-KOH solution. The latter reduction method may require an additional step of base neutralization, water washing, and drying before the catalyst is used. If desired, the catalyst may be reduced in situ after being charged to the reactor.

According to a preferred feature of this invention, the catalyst is contacted during the reaction with the dibenzofuran, at the same time the catalyst is contacted during the reaction with a gas stream comprised of hydrogen or hydrogen mixed with water vapor or an inert gas such as nitrogen, argon, or helium. The gases and dibenzofuran may be preheated to reaction temperature prior to being introduced into the reactor containing the heated catalyst and said gases and dibenzofuran may be brought into contact with the catalyst by either upward or downward flow through the catalyst bed. The temperature for this hydrogenolysis operation may be in the range of about 260° C to 500° C, but preferably about 300° C to 500° C, or still more preferably from 350° C to 475° C. At temperatures below about 260° C undesirable hydrogenation reaction may occur and above about 500° C the catalyst life may be decreased.

The hydrogenolysis reaction may be conducted either in the vapor phase or liquid phase, but is preferably carried out under conditions in which the dibenzofuran is in the vapor phase. More particularly, the hydrogenolysis of dibenzofuran to produce orthophenylphenol may be carried out at a pressure in the range of about 0.1 to 140 atmospheres wherein the gas hourly space velocity (GHSV) is controlled to operate in the range of about 1 hr$^{-1}$ to 10,000 hr$^{-1}$ or higher, but preferably in the range of about 0 hr$^{-1}$ to 5000 hr$^{-1}$. The molar ratio of hydrogen to dibenzofuran feed may be in the range of about 0.5:1 to 100:1. It should be understood that for the complete stoichiometric hydrogenolysis of dibenzofuran to produce orthophenylphenol, a molar ratio of 1:1 for hydrogen to dibenzofuran is necessary.

The orthophenylphenol containing stream which is produced by the hydrogenolysis operation may contain orthophenylphenol, unreacted dibenzofuran, hydrogen, and other components depending upon for example, the activity of the catalyst and the reaction conditions may then be subjected to an operation in which those components such as hydrogen which are normally gases may be separated from those components such as orthophenylphenol which may be liquids by conventional means such as a gas-liquid separator and then directed to various other operations as described in the present invention.

The orthophenylphenol may be recovered from other components by a separation operation which may consist of for example, a conventional distillation. The other components recovered from the separation operation, such as unreacted dibenzofuran for example, may be directed to other positions of the process such as recycling the dibenzofuran back to the inlet of the hydrogenolysis reactor.

The following examples are given to illustrate the process of the present invention, and are not intended to limit the generally broad scope of the present invention. It should be apparent that the particular embodiments chosen to illustrate the invention are not all inclusive and that many changes and variations could be made therein, some of which for example depend upon the activity of the particular catalyst and upon the nature of the starting material. All such changes, modifications, variations or the like, however, which will be apparent to those skilled in the art after considering this disclosure and which do not depart from the spirit and scope of the invention are deemed to be covered by the subjoined claims.

The data in Table 1 show that orthophenylphenol may be produced in a process wherein phenol is converted into orthophenylphenol in a two-step process in which the dibenzofuran is an intermediate. It is also shown in Table 1 that orthophenylphenol may be produced in a process wherein diphenyl ether is converted into orthophenylphenol in a two-stage process in which dibenzofuran is an intermediate. The process operates satisfactorily with the two recycle streams as shown, or with only one of the recycle streams.

TABLE 1

| DESCRIPTION | RUN 1 | RUN 2 | RUN 3 | RUN 4 | RUN 5 |
|---|---|---|---|---|---|
| FEEDSTOCK | PHENOL | PHENOL | DIPHENYL ETHER | DIPHENYL ETHER | PHENOL |
| PROCESS CONDITIONS | | | | | |
| OPERATION 10 | | | | | |
| TEMPERATURE (°C) | 525 | 532 | 562 | 495 | 511 |
| PRESSURE (ATM) | 1 | 1 | 1 | 1 | 1 |
| GHSV (HR$^{-1}$) | 40 | 47 | 52 | 25 | 42 |
| CATALYST ANALYSIS (WT%) | 99.9 Ceria | 92 Ceria 8($Nd_2O_3+Pr_2O_3$) | 99.9 Ceria | 75 Ceria 25 Thoria | 99.9 Ceria |
| OPERATION 21 | | | | | |
| TEMPERATURE (°C) | 400 | 417 | 400 | 400 | 450 |
| PRESSURE (ATM) | 7 | 6 | 7 | 7 | 8.5 |
| GHSV (HR$^{-1}$) | 400 | 590 | 2300 | 400 | 625 |
| CATALYST ANALYSIS (WT%) | 0.1%Pt/$Al_2O_3$ | 0.5%Pd/MgO | 0.5%Pd/MgO | 1.1% Pt/$Al_2O_3$ | 0.5%Pt/MgO |
| FLOW RATES (KG HR$^{-1}$) | | | | | |
| LINE 101 | 85 | 133 | 77 | 131 | 91 |
| 111 | 56 | 27 | 84 | 82 | 51 |
| 105 | 141 | 160 | 161 | 223 | 142 |
| 121 | 134 | 155 | 56 | 77 | 85 |
| 109 | 0.6 | 0.8 | 0.3 | 0.3 | 0.5 |
| 203 | 163 | 127 | 98 | 163 | 172 |
| 201 | 0.2 | 0.4 | 1.1 | 0.2 | 0.4 |
| 210 | 47 | 61 | 38 | 47 | 47 |
| 207 | 107 | 73 | 61 | 101 | 79 |

What is claimed is:

1. A process for producing orthophenylphenol which comprises; (a) contacting phenol under dehydration and dehydrogenation conditions with a dehydration-dehydrogenation catalyst; (b) separating the resultant dehydration-dehydrogenation mixture to remove an essentially dibenzofuran stream; (c) recycling a major portion of the unconverted phenol to the dehydration-dehydrogenation step; (d) commingling the essentially dibenzofuran stream with hydrogen; (e) subjecting the resulting dibenzofuran-hydrogen mixture to hydrogenolysis by contact with a hydrogenolysis catalyst under hydrogenolysis conditions; (f) separating the resultant hydrogenolysis mixture to yield an essentially orthophenylphenol stream; and (g) recycling a major portion of the unconverted dibenzofuran to the hydrogenolysis step.

2. A process for producing orthophenylphenol which comprises; (a) contacting phenol under dehydration and dehydrogenation conditions with a dehydration-dehydrogenation catalyst; (b) separating the resultant dehydration-dehydrogenation mixture to remove an essentially dibenzofuran stream; (c) commingling the essentially dibenzofuran stream with hydrogen; (d) subjecting the resulting dibenzofuran-hydrogen mixture to hydrogenolysis by contact with a hydrogenolysis catalyst under hydrogenolysis conditions; (e) separating the resultant hydrogenolysis mixture to yield an essentially orthophenylphenol stream; and (f) recycling a major portion of the unconverted dibenzofuran to the hydrogenolysis step.

3. A process for producing orthophenylphenol which comprises; (a) contacting phenol under dehydration and dehydrogenation conditions with a dehydration-dehydrogenation catalyst; (b) separating the resultant dehydration-dehydrogenation mixture to remove an essentially dibenzofuran stream; (c) recycling a major portion of the unconverted phenol to the dehydration-dehyrogenation step; (d) commingling the essentially dibenzofuran stream with hydrogen; (e) subjecting the resulting dibenzofuran-hydrogen mixture to hydrogenolysis by contact with a hydrogenolysis catalyst under hydrogenolysis conditions; and (f) separating the resultant hydrogenolysis mixture to yield an essentially orthophenylphenol stream.

4. The process of claim 1 further characterized in that said dehydration-dehydrogenation is catalyzed by a member selected from the class consisting of ceria and combinations of ceria with an oxide of metal of the group consisting of aluminum, silicon, magnesium, titanium, zirconium, hafnium, calcium, potassium, sodium, lanthanum, neodymium, praseodymium, samarium, thorium, and uranium and mixtures thereof.

5. The process of claim 1 further characterized in that said hydrogenolysis is catalyzed by a catalyst composed essentially of a Group VIII element.

6. Process as in claim 1 in which the dehydration-dehydrogenation is carried out in the vapor phase at a temperature of 300° C to 700° C.

7. Process as in claim 1 in which the hydrogenolysis is carried out in the vapor phase at a temperature of 300° C to 500° C.

8. A process for producing orthophenylphenol which comprises: (a) contacting diphenyl ether under dehydrogenation conditions with a dehydrogenation catalyst; (b) fractionating the resultant dehydrogenation mixture to separate an essentially dibenzofuran stream; (c) recycling a major portion of the unconverted diphenyl ether to the dehydrogenation step; (d) commingling the essentially dibenzofuran stream with hydrogen; (e) subjecting the resulting dibenzofuran-hydrogen mixture to hydrogenolysis by contact with a hydrogenolysis catalyst under hydrogenolysis conditions; (f) separating resultant hydrogenolysis mixture to yield an essentially orthophenylphenol stream; and (g) recycling a major portion of the unconverted dibenzofuran to the hydrogenolysis step.

9. A process for producing orthophenylphenol which comprises: (a) contacting diphenyl ether under dehydrogenation conditions with a dehydrogenation catalyst; (b) fractionating the resultant dehydrogenation mixture to separate an essentially dibenzofuran stream; (c) commingling the essentially dibenzofuran stream with hydrogen; (d) subjecting the resulting dibenzofuran-hydrogen mixture to hydrogenolysis by contact with a hydrogenolysis catalyst under hydrogenolysis conditions; (e) separating the resultant hydrogenolysis mixture to yield an essentially orthophenylphenol stream; and (f) recycling a major portion of the unconverted dibenzofuran to the hydrogenolysis step.

10. A process for producing orthophenylphenol which comprises: (a) contacting diphenyl ether under dehydrogenation conditions with a dehydrogenation catalyst; (b) fractionating the resultant dehydrogenation mixture to separate an essentially dibenzofuran stream; (c) recycling a major portion of the unconverted diphenyl ether to the dehydrogenation step; (d) commingling the essentially dibenzofuran stream with hydrogen; (e) subjecting the resulting dibenzofuran-hydrogen mixture to hydrogenolysis by contact with a hydrogenolysis catalyst under hydrogenolysis conditions; and (f) separating the resultant hydrogenolysis mixture to yield an essentially orthophenylphenol stream.

11. The process of claim 8 further characterized in that said dehydration-dehydrogenation is catalyzed by a member selected from the class consisting of ceria and combinations of ceria with an oxide of metal of the group consisting of aluminum, silicon, magnesium, titanium, zirconium, hafnium, calcium, potassium, sodium, lanthanum, neodymium, praseodymium, samarium, thorium, and uranium and mixtures thereof.

12. The process of claim 8 further characterized in that said hydrogenolysis is catalyzed by a catalyst composed essentially of a Group VIII element.

13. Process as in claim 8 in which the dehydration-dehydrogenation is carried out in the vapor phase at a temperature of 300° C to 700° C.

14. Process as in claim 8 in which the hydrogenolysis is carried out in the vapor phase at a temperature of 300° C to 500° C.

* * * * *